United States Patent
Lee et al.

(10) Patent No.: US 11,291,429 B2
(45) Date of Patent: Apr. 5, 2022

(54) MEDICAL IMAGING APPARATUS AND METHOD OF GENERATING MEDICAL IMAGE

(71) Applicant: SAMSUNG MEDISON CO., LTD., Hongcheon-gun (KR)

(72) Inventors: Su-myeong Lee, Hongcheon-gun (KR); Yong-ho Lee, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 568 days.

(21) Appl. No.: 15/997,935

(22) Filed: Jun. 5, 2018

(65) Prior Publication Data
US 2018/0303462 A1 Oct. 25, 2018

Related U.S. Application Data

(62) Division of application No. 14/739,147, filed on Jun. 15, 2015, now abandoned.

(Continued)

(30) Foreign Application Priority Data

Dec. 9, 2014 (KR) .................. 10-2014-0175876

(51) Int. Cl.
*A61B 8/08* (2006.01)
*A61B 8/00* (2006.01)
*A61B 8/06* (2006.01)

(52) U.S. Cl.
CPC .......... *A61B 8/5207* (2013.01); *A61B 8/4427* (2013.01); *A61B 8/461* (2013.01);
(Continued)

(58) Field of Classification Search
CPC ....... A61B 8/52; A61B 8/5246; A61B 8/4427; A61B 8/461; A61B 8/465; A61B 8/469;
(Continued)

(56) References Cited

U.S. PATENT DOCUMENTS 4,559,952 A * 12/1985 Angelsen ................. A61B 8/13
600/455
5,476,097 A * 12/1995 Robinson ................. A61B 8/06
600/441

(Continued)

FOREIGN PATENT DOCUMENTS

CN 101664323 A 3/2010
CN 102414575 A 4/2012
(Continued)

OTHER PUBLICATIONS

Communication dated Jul. 24, 2019 issued by the State Intellectual Property Office of P.R. China in counterpart Chinese Application No. 201510309238.7.

(Continued)

*Primary Examiner* — Sean D Mattson
(74) *Attorney, Agent, or Firm* — Sughrue Mion, PLLC

(57) ABSTRACT

Provided are a medical imaging apparatus and a method of generating a medical image that are capable of generating a Doppler image by using a Doppler effect as well as an ultrasound image. The method of generating a medical image includes: acquiring received signals; acquiring an ultrasound image and displaying the acquired ultrasound image; acquiring a Doppler signal corresponding to a sample volume set on the ultrasound image; generating a Doppler image based on the Doppler signal and displaying the generated Doppler image; calculating at least one selected from an average magnitude, a maximum value, and a minimum value of the Doppler signal; and changing image displaying mode by suspending the displaying of the Doppler image and updating the ultrasound image, in response to the at least one selected from the average magnitude, the maximum value, and the minimum value is less than or equal to a threshold value thereof.

8 Claims, 11 Drawing Sheets

Related U.S. Application Data

(60) Provisional application No. 62/044,373, filed on Sep. 1, 2014.

(52) U.S. Cl.
CPC .............. *A61B 8/465* (2013.01); *A61B 8/469* (2013.01); *A61B 8/488* (2013.01); *A61B 8/5246* (2013.01); *A61B 8/06* (2013.01); *A61B 8/4472* (2013.01); *A61B 8/464* (2013.01); *A61B 8/483* (2013.01)

(58) Field of Classification Search
CPC ......... A61B 8/488; A61B 8/06; A61B 8/4472; A61B 8/464; A61B 8/483; A61B 8/00; A61B 8/40; A61B 8/403; A61B 8/463
See application file for complete search history.

(56) References Cited

U.S. PATENT DOCUMENTS

| | | | |
|---|---|---|---|
| 6,086,539 | A | 6/2000 | Guracar et al. |
| 8,162,837 | B2 * | 4/2012 | Moehring ........... G01S 7/52066 600/454 |
| 8,353,835 | B2 | 1/2013 | Kim et al. |
| 9,078,590 | B2 | 7/2015 | Kim et al. |
| 2002/0173721 | A1 | 11/2002 | Grunwald et al. |
| 2006/0170714 | A1 | 8/2006 | Kanda |
| 2007/0016050 | A1 * | 1/2007 | Moehring .............. A61B 5/725 600/454 |
| 2007/0167790 | A1 | 7/2007 | Kim et al. |
| 2008/0114240 | A1 | 5/2008 | Sasaki |
| 2008/0269605 | A1 * | 10/2008 | Nakaya ................ A61B 5/6844 600/437 |
| 2009/0015587 | A1 | 1/2009 | Hashimoto et al. |
| 2012/0059262 | A1 * | 3/2012 | Clark .................. G01S 7/52084 600/440 |
| 2013/0123603 | A1 | 5/2013 | Shin |
| 2013/0178743 | A1 | 7/2013 | Shim et al. |
| 2014/0098049 | A1 | 4/2014 | Koch et al. |
| 2015/0222838 | A1 | 8/2015 | Kawabata et al. |

FOREIGN PATENT DOCUMENTS

| | | |
|---|---|---|
| CN | 102793565 A | 11/2012 |
| CN | 103099676 A | 5/2013 |
| CN | 103190931 A | 7/2013 |
| EP | 1 798 573 A2 | 6/2007 |
| EP | 1 977 694 A1 | 10/2008 |
| JP | 2-4350 A | 1/1990 |
| JP | 7-323028 A | 12/1995 |
| JP | 2007-159923 A | 6/2007 |
| JP | 2007-222390 A | 9/2007 |
| JP | 2008-55101 A | 3/2008 |
| JP | 2011-83525 A | 4/2011 |
| KR | 10-2008-0018444 A | 2/2008 |
| KR | 10-2011-0044812 A | 5/2011 |
| KR | 10-2012-0062952 A | 6/2012 |

OTHER PUBLICATIONS

Communication dated Jan. 8, 2016 issued by the European Patent Office in counterpart European Patent Application No. 15166129.5.
Communication dated Dec. 7, 2015 issued by the Korean Intellectual Property Office in counterpart Korean Patent Application No. 10-2014-0175876.
Communication dated Jun. 22, 2016 issued by the Korean Intellectual Property Office in counterpart Korean Patent Application No. 10-2014-0175876.
Communication dated Sep. 7, 2016 issued by the Korean Intellectual Property Office in counterpart Korean Patent Application No. 10-2014-0175876.
Communication issued by the Korean Intellectual Property Office dated Jul. 27, 2017 in counterpart Korean Patent Application No. 10-2014-0175876.

* cited by examiner

MEDICAL IMAGING APPARATUS AND METHOD OF GENERATING MEDICAL IMAGE

CROSS-REFERENCE TO RELATED APPLICATIONS

This application is a divisional of U.S. application Ser. No. 14/739,147, filed on Jun. 15, 2015, which claims the benefit of U.S. Provisional Application No. 62/044,373, filed on Sep. 1, 2014, in the U.S. Patent and Trademark Office and Korean Patent Application No. 10-2014-0175876, filed on Dec. 9, 2014, in the Korean Intellectual Property Office, the disclosures of which are incorporated by reference herein in their entireties.

BACKGROUND

1. Field

One or more exemplary embodiments relate to a medical imaging apparatus and a method of generating a medical image, and more particularly, to a medical imaging apparatus and a method of generating a medical image, which are capable of generating a Doppler image by using a Doppler effect as well as an ultrasound image.

2. Description of the Related Art

A medical imaging apparatus for providing an image generated using ultrasound waves may be referred to as an 'ultrasound diagnosis apparatus'. Ultrasound diagnosis apparatuses transmit ultrasound signals generated by transducers of a probe to an object and receive echo signals reflected from the object, thereby obtaining at least one image of an internal area of the object. In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to the lack of radiation exposure, compared to X-ray apparatuses. Therefore, an ultrasound diagnosis apparatus is widely used together with other types of imaging diagnosis devices.

An ultrasound diagnosis apparatus may perform a Doppler scan, which is a technique for obtaining information about a moving substance such as blood within an object based on ultrasound Doppler principles. The ultrasound diagnosis apparatus generally uses a method including performing Pulsed Wave (PW) Doppler or Color Doppler and observing temporal changes in Doppler information.

According to a PW Doppler method, a user may designate a location (i.e., a sample volume) where a Doppler signal is to be acquired on an ultrasound image such as a B-mode image displayed on an ultrasound diagnosis apparatus. Then, an ultrasound pulse is transmitted to the designated location and focused thereon. In PW Doppler, to measure movement of a high-velocity substance, repetitive pulse frequency (RPF) that is the cycle of alternating transmission and reception of ultrasound pulses must be increased.

According to a conventional method of providing a user with a Doppler image, first, an ultrasound diagnosis apparatus generates an ultrasound image showing a wide range of tissues including Doppler scan tissue, e.g., by operating in a B-mode. Thereafter, to perform a Doppler scan, the ultrasound diagnosis apparatus suspends generation of an ultrasound image. In this case, the ultrasound diagnosis apparatus displays an ultrasound image generated prior to the suspension as a reference image. A user may use the ultrasound image to designate a location (i.e., sample volume) where a Doppler signal is to be acquired. If the user sets on an ultrasound image a location (i.e., a sample volume) where a Doppler signal will be acquired, the ultrasound diagnosis apparatus consecutively repeats a Doppler scan so that an ultrasound pulse is focused at the designated location. In other words, the ultrasound diagnosis apparatus operates in a Doppler (D) only mode.

However, in the conventional method, since generation of an ultrasound image is suspended during a Doppler scan, an ultrasound diagnosis apparatus may display a previously generated ultrasound image. Thus, it is difficult to display a sample volume marker indicating a location where a Doppler scan is performed in a real-time image. Due to this limitation, if a location of Doppler scan tissue is moved, to modify a location where the Doppler scan is performed, a user is inconvenienced by having to move a location of a sample volume after performing a user input for changing an operating mode to a mode in which the ultrasound diagnosis apparatus generates an ultrasound image.

SUMMARY

One or more exemplary embodiments include a medical imaging apparatus and a method of generating a medical image, which allow a user to easily set a location of a sample volume on an ultrasound image.

Additional aspects will be set forth in part in the description which follows and, in part, will be apparent from the description, or may be learned by practice of the presented exemplary embodiments.

According to one or more exemplary embodiments, a method of generating a medical image by using a medical imaging apparatus includes: acquiring received signals; acquiring an ultrasound image and displaying the acquired ultrasound image; acquiring a Doppler signal corresponding to a sample volume that is set on the ultrasound image, based on the received signals; generating a Doppler image based on the Doppler signal and displaying the generated Doppler image; receiving a user input for moving a location of the sample volume; and suspending, if the user input is received, the displaying of the Doppler image and updating the ultrasound image.

The Doppler image may include at least one of a color Doppler image and a Pulsed Wave (PW) Doppler image.

In the updating of the ultrasound image, if a time period during which the user input is not received is greater than or equal to a threshold value, the displaying of the Doppler image is repeated.

The method may further include setting the threshold value.

The user input may be received via at least one selected from a track ball, a mouse, and a touch panel included in the medical imaging apparatus.

According to one or more exemplary embodiments, a method of generating a medical image by using a medical imaging apparatus includes: acquiring received signals; acquiring an ultrasound image and displaying the acquired ultrasound image; acquiring a Doppler signal corresponding to a sample volume set on the ultrasound image; generating a Doppler image based on the Doppler signal and displaying the generated Doppler image; calculating at least one selected from an average magnitude, a maximum value, and a minimum value of the Doppler signal; and suspending, if the at least one selected from the average magnitude, the maximum value, and the minimum value is less than or equal to a threshold value thereof, the displaying of the Doppler image and updating the ultrasound image.

The Doppler image may include at least one of a color Doppler image and a PW Doppler image.

The updating of the ultrasound image may include determining if the Doppler signal is included in the received signals; and suspending, if the Doppler signal is included in the received signals, the updating of the ultrasound image and the displaying of the Doppler image again.

According to one or more exemplary embodiments, a medical imaging apparatus includes an input device configured to receive a user input for determining a location of a sample volume on an ultrasound image; an ultrasound transceiver configured to transmit ultrasound signals to an object and receive ultrasound echo signals reflected from the object; a data processor configured to acquire received signals based on the ultrasound echo signals received by the ultrasound transceiver, select a Doppler signal corresponding to a sample volume set on the ultrasound image from among the received signals, and generate Doppler data based on the Doppler signal; and an image generator configured to generate a Doppler image based on the Doppler data, wherein, if the user input is received via the input device, the data processor suspends generation of the Doppler data, selects a received signal for generating an ultrasound image from among the received signals, and updates the ultrasound image based on the received signal for generating the ultrasound image.

The Doppler image may include at least one of a color Doppler image and a PW Doppler image.

If a time period during which the user input is not received is greater than or equal to a threshold value, the data processor may suspend the updating of the ultrasound image and generates the Doppler data again.

The data processor may set the threshold value based on a user input.

The input device may include at least one selected from a track ball, a mouse, and a touch panel included in the medical imaging apparatus.

If the Doppler signal included in the received signals is recognized while the ultrasound image is being updated, the data processor may suspend the updating of the ultrasound image and generates the Doppler data again.

According to one or more exemplary embodiments, a medical imaging apparatus includes: an ultrasound transceiver configured to transmit ultrasound signals to an object and receive ultrasound echo signals reflected from the object; a data processor configured to acquire received signals based on the ultrasound echo signals received from the ultrasound transceiver, select a Doppler signal corresponding to a sample volume set on the ultrasound image from among the received signals, and generate Doppler data based on the Doppler signal; and an image generator configured to generate a Doppler image based on the Doppler data, wherein, if at least one selected from an average magnitude, a maximum value, and a minimum value is less than or equal to a threshold value thereof, the data processor suspends generation of the Doppler data, selects a received signal for generating an ultrasound image from among the received signals, and updates the ultrasound image based on the received signal for generating the ultrasound image.

The Doppler image may include at least one of a color Doppler image and a PW Doppler image.

According to one or more exemplary embodiments, a non-transitory computer-readable recording medium has recorded thereon a program for executing the above-described methods on a computer.

The method and apparatus according to the one or more exemplary embodiments allow a user to easily set at least one of a location and a region where a Doppler image is to be acquired in an ultrasound image.

Furthermore, according to the one or more exemplary embodiments, information about a fast moving object such as blood flow may be obtained while allowing a user to easily set at least one from among a location and a region where a Doppler image is to be acquired in an ultrasound image.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
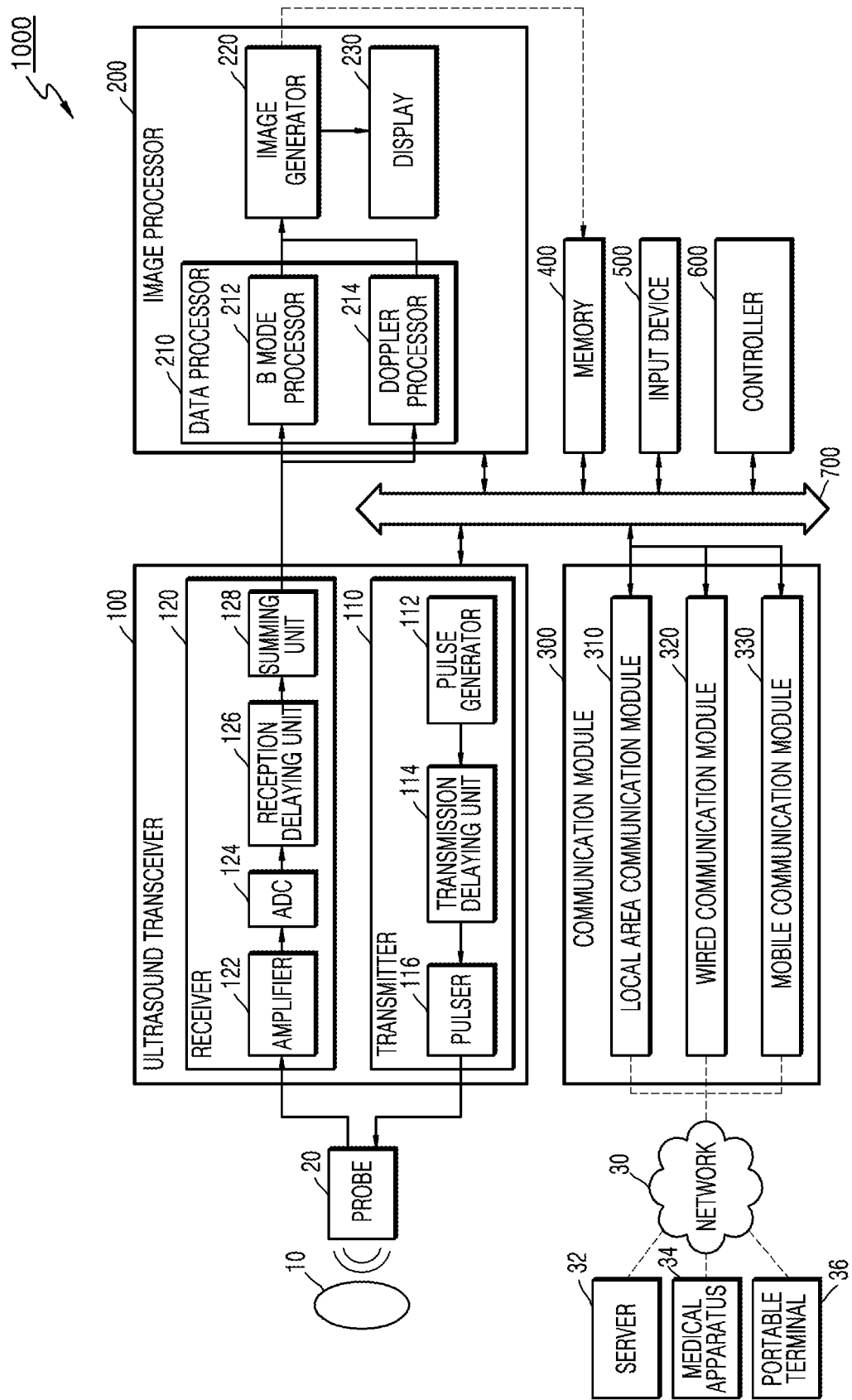
FIG. 1 is a block diagram of a configuration of an ultrasound diagnosis apparatus related to an exemplary embodiment.

Exemplary embodiments will now be described more fully hereinafter with reference to the accompanying drawings so that they may be easily implemented by one of ordinary skill in the art. However, the present embodiments may have different forms and should not be construed as being limited to the descriptions set forth herein. In addition, parts not related to the present inventive concept are omitted to clarify the description of exemplary embodiments. In the accompanying drawings, like reference numerals refer to like elements throughout. Expressions such as "at least one of," when preceding a list of elements, modify the entire list of elements and do not modify the individual elements of the list.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, it will be understood that when an element is referred to as being "connected" or "coupled" to another element, it can be directly connected to or electrically coupled to the other element with one or more intervening elements interposed therebetween.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Furthermore, an "ultrasound diagnosis apparatus" may be merely an example of a medical imaging apparatus, but a medical imaging apparatus is not limited thereto. For example, the medical imaging apparatus may be formed by software, hardware such as a Picture Archiving Communication System (PACS) or portable computer, or a combination thereof.

Exemplary embodiments will now be described with reference to the accompanying drawings.

FIG. 1 is a block diagram showing a configuration of an ultrasound diagnosis apparatus 1000 according to an embodiment. Referring to FIG. 1, the ultrasound diagnosis apparatus 1000 may include a probe 20, an ultrasound transceiver 100, an image processor 200, a communication module 300, a display 600, a memory 400, an input device 500, and a controller 600, which may be connected to one another via buses 700.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 166. In some embodiments, the receiver 120 may not include the amplifier 122. In other words, if the sensitivity of the probe 20 or the capability of the ADC 124 to process bits is enhanced, the amplifier 122 may be omitted.

The image processor 200 generates an ultrasound image by scan-converting ultrasound data generated by the ultrasound transceiver 100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may include at least one selected from a blood flow Doppler image showing flow of blood (also referred to as a color Doppler image), a tissue Doppler image showing a movement of tissue, a spectral Doppler image showing a moving speed of an object as a waveform, and a pulsed wave (PW) Doppler image.

A B mode processor 212 extracts B mode components from ultrasound data and processes the B mode components. An image generator 220 may generate an ultrasound image indicating signal intensities as brightness based on the extracted B mode components.

Similarly, a Doppler processor 214 may extract Doppler components (that is, Doppler data) from ultrasound data, and the image generator 220 may generate a Doppler image indicating a movement of an object as colors or waveforms based on the extracted Doppler components.

According to an embodiment, the image generator 220 may generate a three-dimensional (3D) ultrasound image via volume-rendering with respect to volume data and may also generate an elasticity image by imaging deformation of the object 10 due to pressure. Furthermore, the image generator 220 may display various pieces of additional information in an ultrasound image by using text and graphics. In addition, the generated ultrasound image may be stored in the memory 400.

A display 230 displays the generated ultrasound image. The display 230 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 230 according to embodiments.

The communication module 300 is connected to a network 30 by wire or wirelessly to communicate with an external device or a server. The communication module 300 may exchange data with a hospital server or another medical apparatus in a hospital, which is connected thereto via a PACS. Furthermore, the communication module 300 may perform data communication according to the digital imaging and communications in medicine (DICOM) standard.

The communication module 300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 300 may receive information about a diagnosis history or medical treatment schedule of a patient from a server and utilizes the received information to diagnose the patient. Furthermore, the communication module 300 may perform data communication not only with a server or a medical apparatus in a hospital, but also with a portable terminal of a medical doctor or patient.

The communication module 300 is connected to the network 30 by wire or wirelessly to exchange data with a server 32, a medical apparatus 34, or a portable terminal 36. The communication module 300 may include one or more components for communication with external devices. For example, the communication module 1300 may include a local area communication module 310, a wired communication module 320, and a mobile communication module 330.

The local area communication module 310 refers to a module for local area communication within a predetermined distance. Examples of local area communication techniques according to an embodiment may include, but are not limited to, wireless LAN, Wi-Fi, Bluetooth, zigbee, Wi-Fi Direct (WFD), ultra wideband (UWB), infrared data association (IrDA), Bluetooth low energy (BLE), and near field communication (NFC).

The wired communication module 320 refers to a module for communication using electric signals or optical signals. Examples of wired communication techniques according to an embodiment may include communication via a twisted pair cable, a coaxial cable, an optical fiber cable, and an Ethernet cable.

The mobile communication module 330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 400 stores various data processed by the ultrasound diagnosis apparatus 1000. For example, the memory 400 may store medical data related to diagnosis of an object, such as ultrasound data and an ultrasound image that are input or output, and may also store algorithms or programs which are to be executed in the ultrasound diagnosis apparatus 1000.

The memory 400 may be any of various storage media, e.g., a flash memory, a hard disk drive, EEPROM, etc. Furthermore, the ultrasound diagnosis apparatus 1000 may utilize web storage or a cloud server that performs the storage function of the memory 400 online.

The input device 500 refers to a means via which a user inputs data for controlling the ultrasound diagnosis apparatus 1000. The input device 500 may include hardware components, such as a keypad, a mouse, a touch panel, a touch screen, and a jog switch. However, embodiments are not limited thereto, and the input device 500 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 600 may control all operations of the ultrasound diagnosis apparatus 1000. In other words, the controller 600 may control operations among the probe 20, the ultrasound transceiver 100, the image processor 200, the communication module 300, the memory 400, and the input device 500 shown in FIG. 1.

All or some of the probe 20, the ultrasound transceiver 100, the image processor 200, the communication module 300, the memory 400, the input device 500, and the controller 600 may be implemented as software modules. However, embodiments of the present invention are not limited thereto, and some of the components stated above may be implemented as hardware modules. Furthermore, at least one selected from the ultrasound transceiver 100, the image processor 200, and the communication module 300 may be included in the controller 600. However, embodiments of the present invention are not limited thereto.

Figure 2:
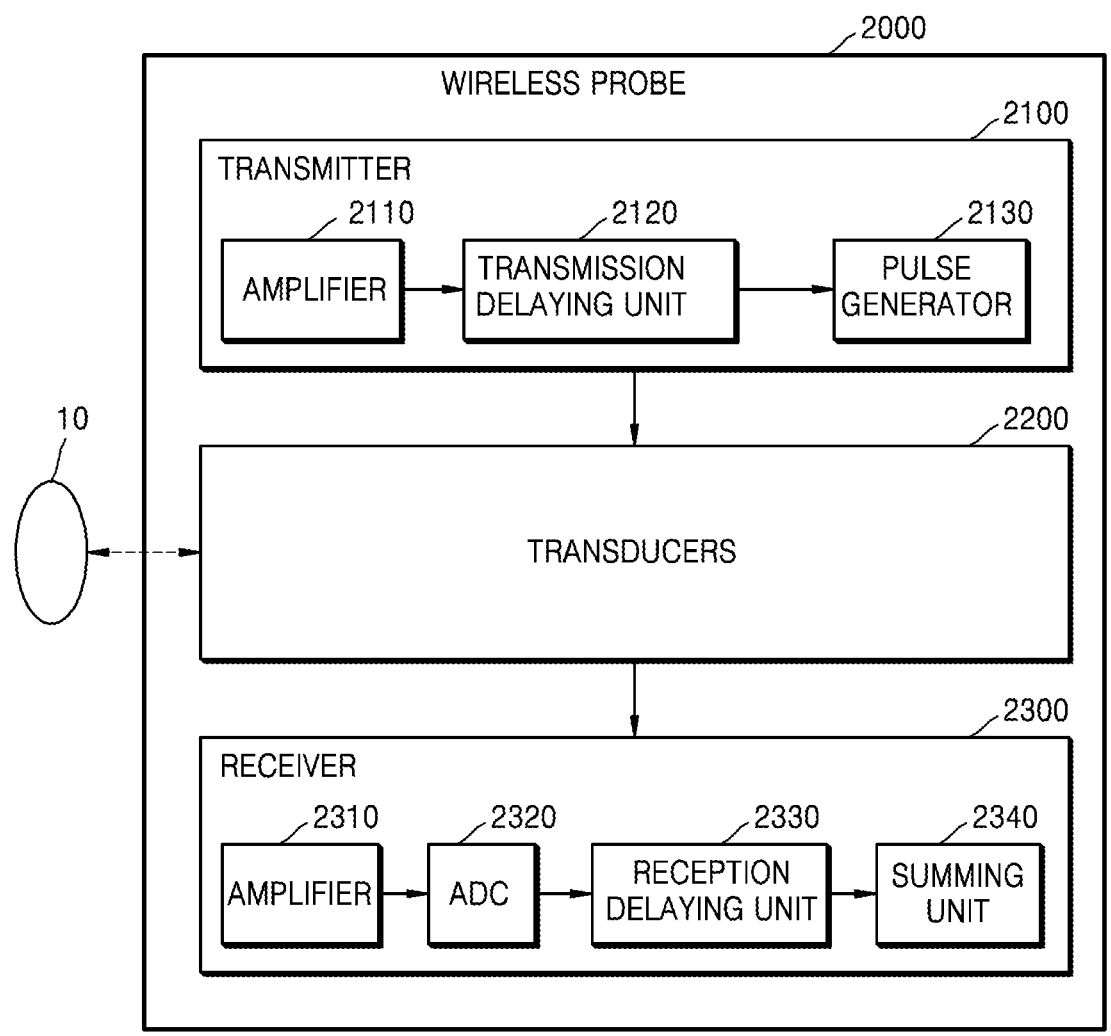
FIG. 2 is a block diagram of a configuration of a wireless probe related to an exemplary embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

Figure 3A:
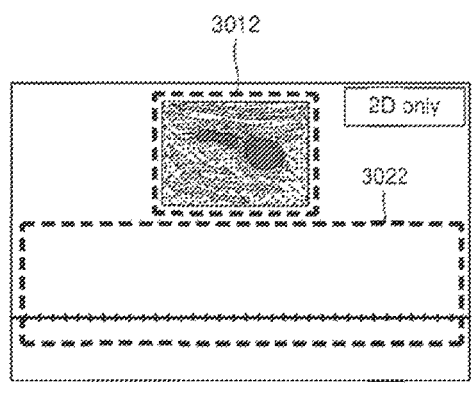
FIG. 3A and FIG. 3B illustrate example of an ultrasound image and a Doppler image displayed on a medical imaging apparatus.
Figure 3B:
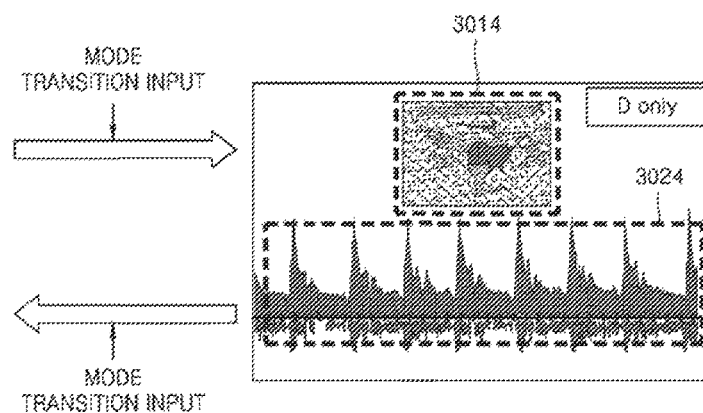

FIGS. 3A and 3B illustrate an example of an ultrasound image and a Doppler image displayed on a medical imaging apparatus.

Referring to FIG. 3A, a user may generate an ultrasound image 3012 encompassing a wide range of tissue. A medical imaging apparatus may display the generated ultrasound image 3012. In this case, a Doppler image 3022 is not generated. Generating and displaying the ultrasound image 3012 means operating in a B-mode. Alternatively, a state in which the medical imaging apparatus generates and displays the ultrasound image 3012 may mean that an operating mode of the medical imaging apparatus is set to a B-mode.

The user may set in the ultrasound image 3012 at least one of a location and a region (e. g., a sample volume) where the user desires to generate a Doppler image. In other words, the medical imaging apparatus may receive an input for setting a location where a Doppler image is to be generated. For example, the user may move a location of a sample volume gate indicating at least one of a location and a region of a sample volume within the ultrasound image 3012 by using a track ball included in the input device (500 of FIG. 1) of the medical imaging apparatus. In other words, the medical imaging apparatus may receive a user input via the input device 500 (e.g., a track ball). Exemplary embodiments are not limited thereto.

After setting the location where the Doppler image is to be generated, the user may input to the medical imaging apparatus a mode transition command for changing an operating mode of the medical imaging apparatus. In other words, the medical imaging apparatus may receive a mode transition input (i.e., a mode transition command). For example, an operating mode of the medical imaging apparatus may change to a Doppler mode by using a button included in the input device 500. Referring to FIG. 3B, when the operating mode of the medical imaging apparatus is in a Doppler mode, the medical imaging apparatus may display an ultrasound image 3014 that was last generated. In other words, when the medical imaging apparatus operates in a Doppler mode, the displayed ultrasound image 3014 may be a still image. Furthermore, when the medical imaging apparatus is set to a Doppler mode, the medical imaging apparatus may generate a Doppler image 3024 for a set sample volume.

The generated Doppler image 3024 may be displayed using the medical imaging apparatus or a separate display. In this case, a location of a sample volume may be moved out of a position intended by the user. For example, a location in an object corresponding to a location of a sample volume in the Doppler image 3024 may not coincide with a position intended by the user due to movement of the object or a probe. In this case, a normal Doppler image is not generated. The user may recognize that the Doppler image generated by the medical imaging apparatus is not normal and input a mode transition command to the medical imaging apparatus. Upon receipt of the mode transition input (i.e., the mode transition command), the medical imaging apparatus may display the ultrasound image 3012 captured in (almost) real-time and the still Doppler image 3022 by operating in a B-mode. Thereafter, the user may modify a location where a Doppler image is to be generated based on the ultrasound image 3012. However, in this case, the user is inconvenienced by having to separately input a mode transition command each time the user changes a location where a Doppler image is to be generated.

When an ultrasound image and a Doppler image are acquired and output simultaneously, but not separately, as shown in FIGS. 3A and 3B, a range of frequencies of a Doppler signal for generating a Doppler image narrows. Thus, when the Doppler image and the ultrasound image are acquired simultaneously, it is difficult to obtain information about a high-velocity object (e.g., blood flow).

Figure 4:
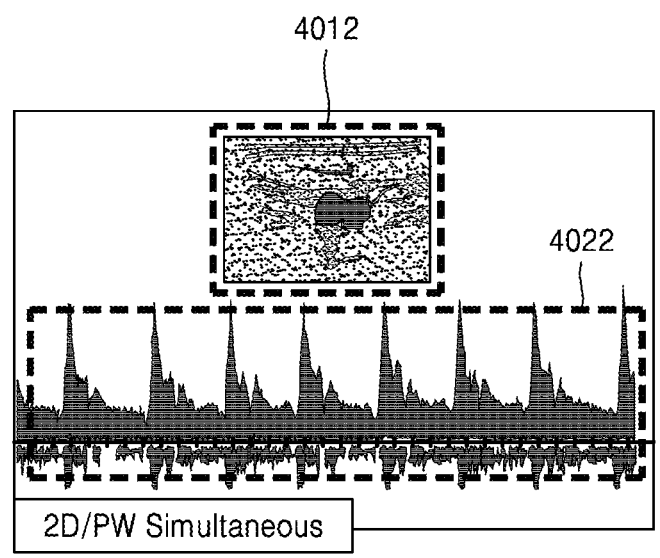
FIG. 4 illustrates an example of an ultrasound image and a Doppler image generated and displayed simultaneously by a medical imaging apparatus according to an exemplary embodiment.

FIG. 4 illustrates an example of an ultrasound image 4012 and a Doppler image 4022 generated and displayed simultaneously by a medical imaging apparatus according to an exemplary embodiment.

The medical imaging apparatus may simultaneously display the ultrasound image 4012 and the Doppler image 4022. The medical imaging apparatus may alternately acquire ultrasound data and Doppler data. The ultrasound image 4012 may be updated each time new ultrasound data is acquired. However, since the Doppler image 4022 is continuously produced and displayed along a time axis, the Doppler image 4022 does not appear during a time interval when ultrasound data is generated. To solve this problem, the medical imaging apparatus may generate virtual Doppler data during generation of an ultrasound image and fill an empty period with the virtual Doppler data, thereby outputting the Doppler image 4022 having no empty period.

However, in this case, a portion of the Doppler image 4022 is not a real Doppler image but a virtual Doppler image. Furthermore, to simultaneously display the ultrasound image 4012 and the Doppler image 4022 as described above, a system needs to be built for the medical imaging apparatus to alternately acquire an ultrasound signal for an ultrasound image and a Doppler signal and generate a virtual Doppler signal. Thus, the cost of building the system may increase.

Figure 5:
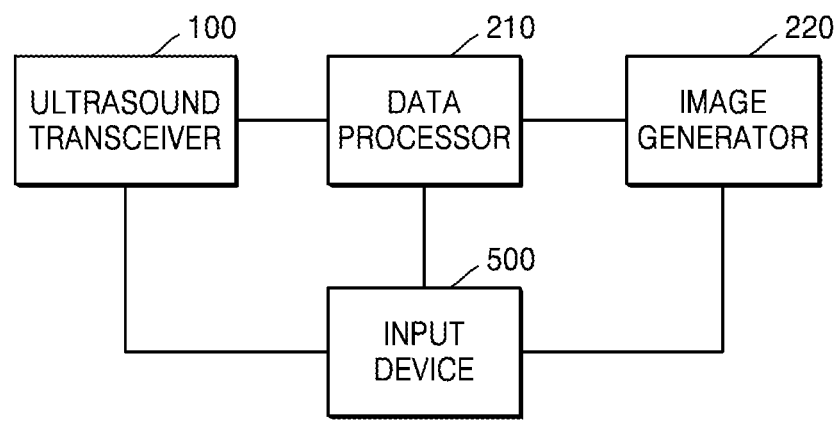
FIG. 5 is a block diagram of a structure of a medical imaging apparatus according to an exemplary embodiment.

FIG. 5 is a block diagram of a structure of a medical imaging apparatus according to an exemplary embodiment.

Referring to FIG. 5, the medical imaging apparatus according to the present exemplary embodiment may include an ultrasound transceiver 100, a data processor 210, an image generator 220, and an input device 500. The components shown in FIG. 5 are merely for explaining an exemplary embodiment, and the medical imaging apparatus of FIG. 5 may include more or fewer components than those shown in FIG. 5.

The ultrasound transceiver 100 may transmit ultrasound signals to an object and receive echo signals reflected from the object via the probe (20 of FIG. 1). Upon receipt of echo signals, the ultrasound transceiver 100 may input the received echo signals to the data processor 210.

The data processor 210 may acquire a received signal based on a signal input from the ultrasound transceiver 100. The data processor 210 may select a received signal for generating an ultrasound image from among received signals. The image generator 220 may generate an ultrasound image based on the selected signal. In this case, the ultrasound image may be an image showing a wide area such as a two-dimensional (2D) B-mode image, color image, or 3D ultrasound image. The generated ultrasound image may be displayed on the display (230 of FIG. 1).

The user may set at least one of a location and a region where a Doppler image is to be acquired, i.e., a sample volume on an ultrasound image, by using the input device 500. After the sample volume is set on the ultrasound image, the data processor 210 may select a Doppler signal for generating a Doppler image from among the received signals. The data processor 210 may also generate Doppler data based on the Doppler signal. The image generator 220 may generate a Doppler image based on the Doppler data. The Doppler image may be a PW Doppler image showing movement of a sample volume, but is not limited thereto. The Doppler image may include at least one selected from a color Doppler image, a power Doppler image, a continuous wave (CW) Doppler image, and an M-mode image. The generated Doppler image may be displayed on the display 230. In this case, the data processor 210 may suspend generation of an ultrasound image. The display 230 may display an ultrasound image that was last generated.

When generating Doppler data, the data processor 210 may suspend generation of the Doppler data and determine whether to generate an ultrasound image. Suspending the generation of the Doppler data and determining whether to generate an ultrasound image (hereinafter, referred to as 'whether to change an operating mode') may be performed in different ways depending on exemplary embodiments.

According to an exemplary embodiment, if a user input is received via the input device 500, the data processor 210 may operate so that generation of a Doppler image is suspended and an ultrasound image is generated (hereinafter, referred to as 'an operating mode is changed'). For example, if a user changes a location or size of a sample volume by using a track ball included in the input device 500, the data processor 210 may suspend generation of Doppler data and transmit ultrasound data for generating an ultrasound image to the image processor 200. Thereafter, if a time period during which a user input is not received is greater than or equal to a threshold value, the data processor 210 may change an operating mode again in order to suspend generation of an ultrasound image and generate a Doppler image. In this case, the threshold value refers to a value that is preset in the medical imaging apparatus or set by the user.

According to another exemplary embodiment, the data processor 210 may determine whether to change an operating mode based on a Doppler signal. For example, if a Doppler signal is acquired from a blood vessel or the heart on an ultrasound image, the data processor 210 may determine whether a value of the Doppler signal (e.g., an average magnitude, a maximum value, a minimum value, a signal intensity, a blood flow velocity, etc.) is out of a normal range. If the value of the Doppler signal is out of the normal range, the data processor 210 may change an operating mode. The normal range may be preset in the medical imaging apparatus or set by a user. Thereafter, if a value of a Doppler signal included in a received signal falls within the normal range (i.e., a Doppler signal included in the received signal is recognized), the data processor 210 may change an operating mode again, i.e., by suspending generation of an ultrasound image and generating a Doppler image.

According to another exemplary embodiment, the data processor 210 may determine whether to change an operating mode based on a signal for generating an ultrasound image, which is included in a received signal. For example, if it is recognized that an ultrasound image moves to a great extent based on the signal for generating an ultrasound image, i.e., if an object or probe moves, a location of a sample volume needs to be changed. In this case, the data processor 210 may change an operating mode so that a displayed ultrasound image is updated.

Figure 6:
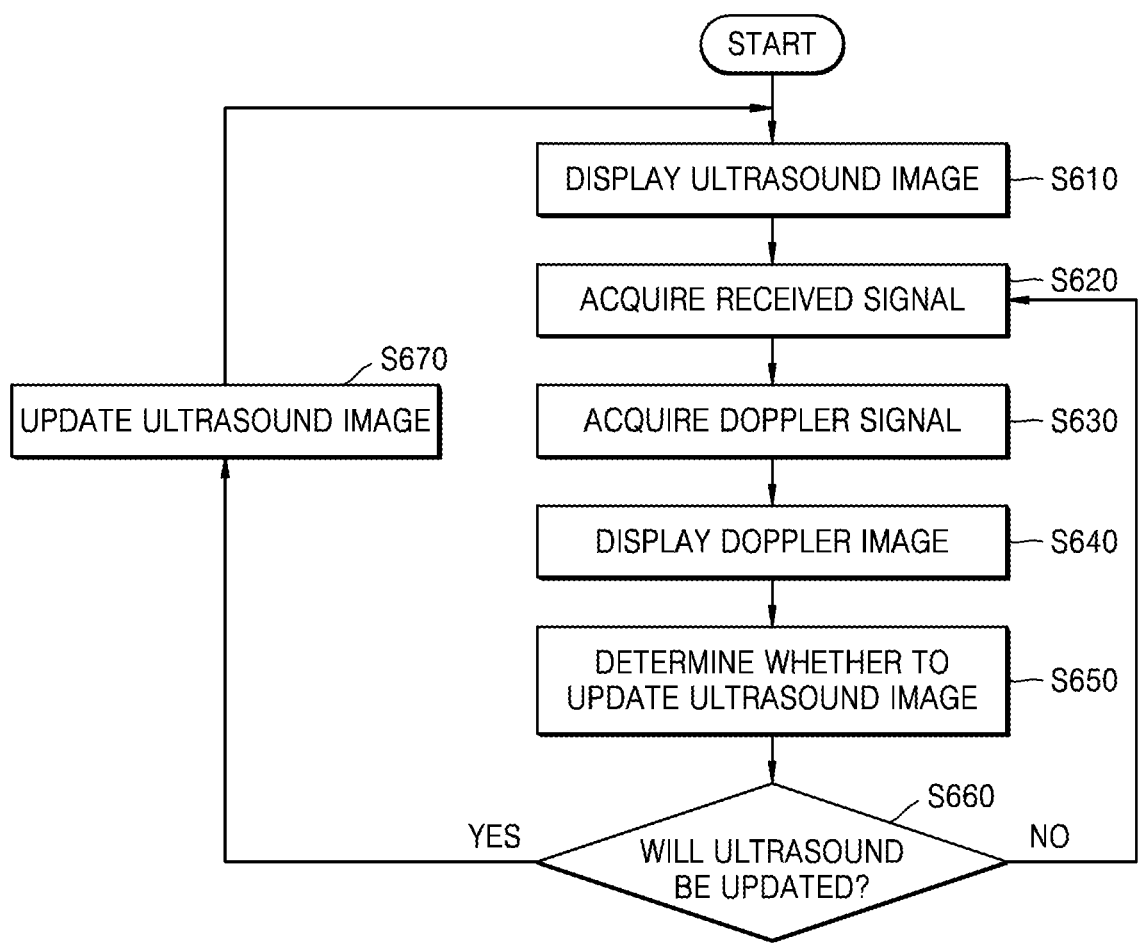
FIG. 6 is a flowchart of a process of generating a medical image, according to an exemplary embodiment.

FIG. 6 is a flowchart of a process of generating a medical image, according to an exemplary embodiment.

Referring to FIG. 6, first, a medical imaging apparatus may display an ultrasound image (S610). In this case, the ultrasound image may include an image depicting a wide area, such as a 2D B-mode image, a color image, or a 3D ultrasound image. After the sample volume is set on the ultrasound image displayed in operation S610, the medical imaging apparatus may acquire a Doppler signal based on a received signal that is acquired in operation S620 (S630).

The medical imaging apparatus may generate Doppler data based on the Doppler signal. The medical imaging apparatus may also display a Doppler image generated based on the Doppler data (S640).

Thereafter, the medical imaging apparatus may determine whether to update an ultrasound image (i.e., whether to change an operating mode) (S650). If the medical imaging apparatus determines that the ultrasound image is to be updated (S660), the medical imaging apparatus may select a received signal for generating an ultrasound image from among the received signals and update the ultrasound image based on the selected received signal (S670). The medical imaging apparatus may display the updated ultrasound image (S610).

On the other hand, if the medical imaging apparatus determines that the ultrasound image is not to be updated from the received signal, the medical imaging apparatus may continuously generate and display a Doppler image in operations S620, S630, and S640.

Figure 7:
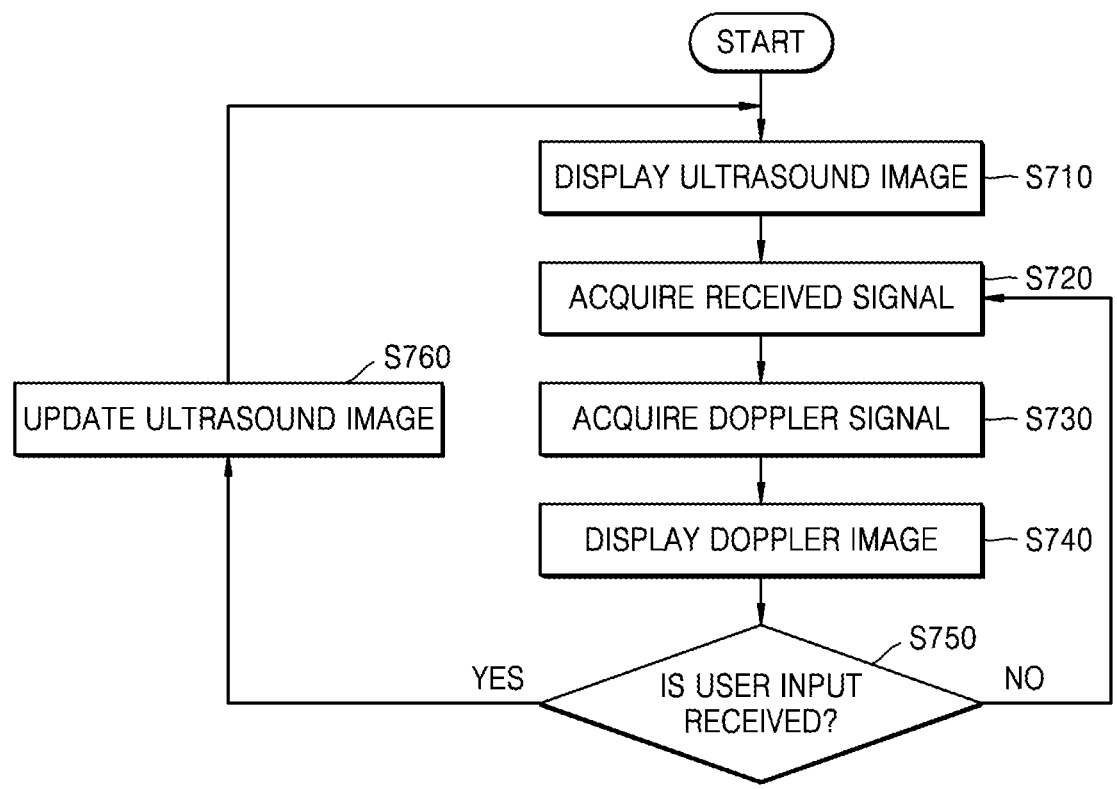
FIG. 7 is a flowchart of a process of generating a medical image based on a user input according to an exemplary embodiment.

FIG. 7 is a flowchart of a process of generating a medical image based on a user input according to an exemplary embodiment.

Referring to FIG. 7, first, a medical imaging apparatus may display an ultrasound image until a sample volume is set (S710). In this case, the ultrasound image may include an image depicting a wide area, such as a 2D B-mode image, a color image, or a 3D ultrasound image. After the sample volume is set on the ultrasound image displayed in operation S710, the medical imaging apparatus may acquire a Doppler signal from received signal that are acquired in operation S720 (S730).

The medical imaging apparatus may generate Doppler data based on the Doppler signal. The medical imaging apparatus may also display a Doppler image generated based on the Doppler data (S740). Thereafter, the medical imaging apparatus may perform operations S760 and S710 until a new sample volume is set.

Then, if a user input (e.g., an input for changing a location or size of a sample volume) is received (S750), the medical imaging apparatus may update an ultrasound image (S760). The medical imaging apparatus may display the updated ultrasound image by performing operations S760 and S710 until a new sample volume is set. For example, the medical imaging apparatus may continuously update an ultrasound image that is displayed until there has been no user input for a predetermined time. In this case, operation S740 is not performed. If the user input is not received in operation S750, the medical imaging apparatus may generate and display a Doppler image in operations S720, S730, and S740.

Figure 8:
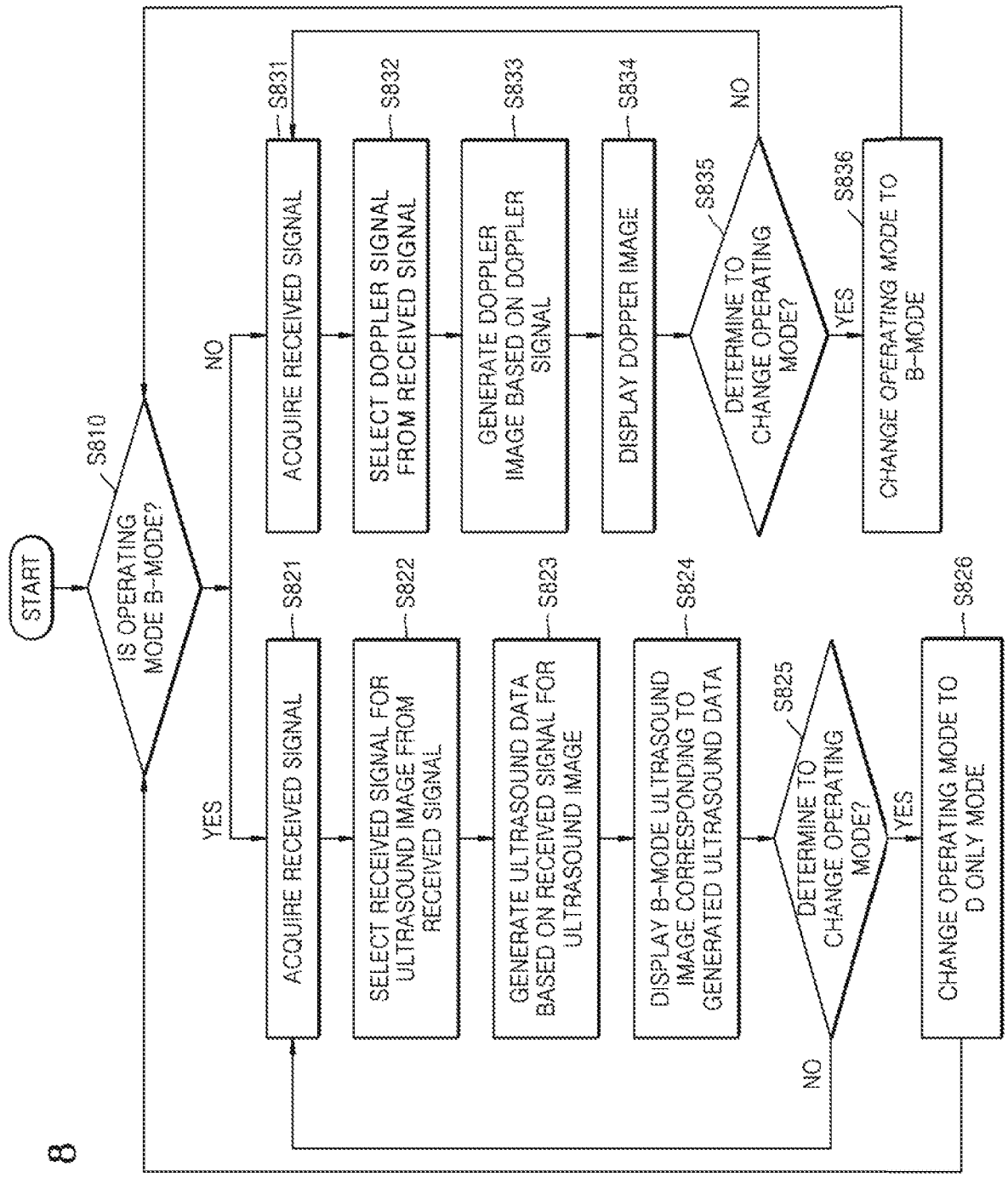
FIG. 8 is a detailed flowchart of a process of generating a medical image based on a user input according to an exemplary embodiment.

FIG. 8 is a detailed flowchart of a process of generating a medical image based on a user input, according to an exemplary embodiment Referring to FIG. 8, first, a medical imaging apparatus may determine an operating mode thereof (S810). If the medical imaging apparatus operates in a B-mode, the medical imaging apparatus acquires received signals (S821). Subsequently, the medical imaging apparatus may select a received signal for generating an ultrasound image from among the acquired received signals (S822). The medical imaging apparatus may then generate ultrasound data based on the received signal for generating an ultrasound image (S823). The medical imaging apparatus may display an ultrasound image corresponding to the generated ultrasound data (S824).

Subsequently, the medical imaging apparatus may determine whether to change an operating mode (S825). For example, the medical imaging apparatus may determine if a time period that elapsed from a time when a user input related to setting of a sample volume is last received is greater than or equal to a threshold value. For example, if one or more seconds elapse after a user moves a location of a sample volume, the medical imaging apparatus may change an operating mode. Otherwise, if the medical imaging apparatus does not change an operating mode, the medical imaging apparatus may display an ultrasound image by repeatedly performing operations S821 to S824. If the medical imaging apparatus determines to change an operating mode in operation S825, the medical imaging apparatus may change the operating mode to a Doppler mode (a D only mode) (S826).

If the medical imaging apparatus operates in a Doppler mode in operation S810, the medical imaging apparatus may acquire received signals (S831) and select a Doppler signal from among the received signals (S832). Subsequently, the medical imaging apparatus may generate a Doppler image based on the Doppler signal (S833). The medical imaging apparatus may then display the generated Doppler image (S834).

Subsequently, the medical imaging apparatus may determine whether to change an operating mode (S835). If the medical imaging apparatus determines to change the operating mode, the medical imaging apparatus may change the operating mode to a mode for generating an ultrasound image (e.g., a B-mode) (S836). For example, the medical imaging apparatus may determine if a user input related to setting of a sample volume is received. If the user moves a location of a sample volume by using a track ball, the medical imaging apparatus may change the operating mode. Thereafter, if the medical imaging apparatus operates in a B-mode in operation S810, the medical imaging apparatus may generate ultrasound data and display an ultrasound image generated based on the generated ultrasound data.

Figure 9:
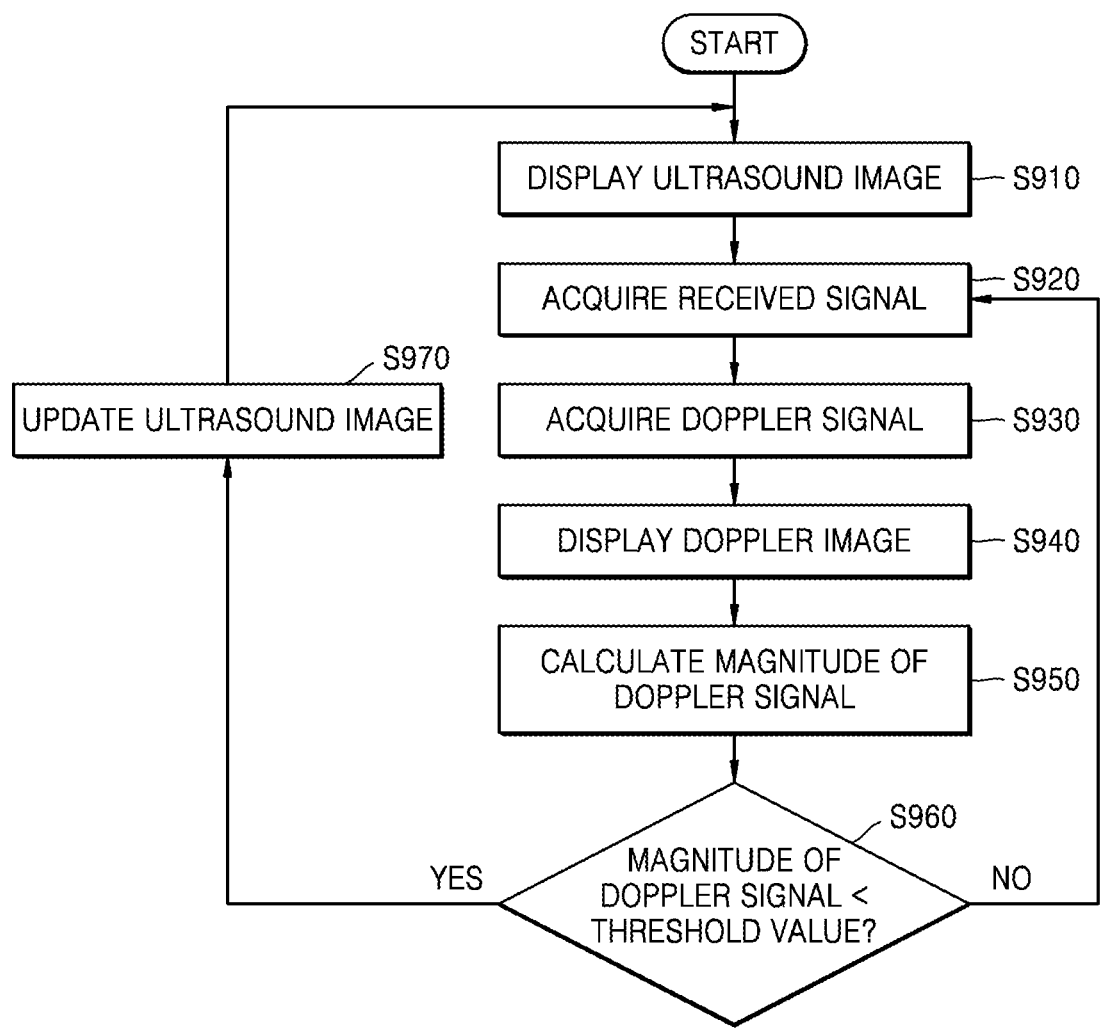
FIG. 9 is a flowchart of a process of generating a medical image based on a Doppler signal according to an exemplary embodiment.

FIG. 9 is a flowchart of a process of generating a medical image based on a Doppler signal according to an exemplary embodiment Referring to FIG. 9, first, a medical imaging apparatus may display an ultrasound image (S910). After a sample volume is set on the ultrasound image displayed in operation S910, the medical imaging apparatus may acquire a Doppler signal from received signals that are acquired in operation S920 (S930).

The medical imaging apparatus may generate Doppler data based on the Doppler signal. The medical imaging apparatus may also display a Doppler image generated based on the Doppler data (S940). Thereafter, the medical imaging apparatus may calculate at least one selected from a magnitude, a maximum value, and a minimum value of the Doppler signal. In this case, the magnitude of the Doppler signal may be an average value of the Doppler signal during a predetermined time interval. Alternatively, the magnitude of the Doppler signal may be a peak value thereof during a predetermined time interval. However, exemplary embodiments are not limited thereto.

The medical imaging apparatus may determine if a calculated magnitude of a Doppler signal falls within a normal range. Referring to FIG. 9, the medical imaging apparatus may determine if the at least one selected from the magnitude, the maximum value, and the minimum value of the Doppler signal is less than a threshold value thereof. For example, the medical imaging apparatus may compare an average magnitude of a Doppler signal against a preset average magnitude thereof. As another example, the medical imaging apparatus may compare a minimum value of the Doppler signal against a preset minimum value thereof. As another example, the medical imaging apparatus may compare a maximum value of the Doppler signal with a preset maximum value thereof. If the at least one selected from the magnitude, the maximum value, and the minimum value of the Doppler signal is greater than the threshold value thereof, the medical imaging apparatus may display the Doppler image by repeating operations S920 to S950. Otherwise, if the at least one selected from the magnitude, the maximum value, and the minimum value of the Doppler signal is less than the threshold value thereof, the medical imaging apparatus may update an ultrasound image (S970) and display the updated ultrasound image. Until the at least one selected from the magnitude, the maximum value, and the minimum value of the Doppler signal becomes greater than or equal to the threshold value thereof, the medical imaging apparatus may suspend display of the Doppler image, update an ultrasound image, and display the updated ultrasound image in operations S970 and S910.

Figures 10A, 10B:
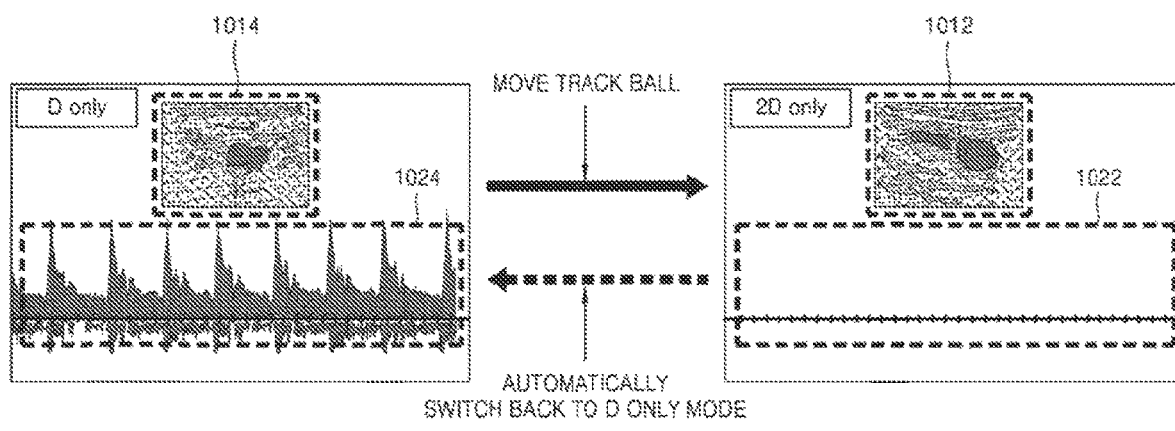
FIGS. 10A and 10B are a diagram showing an example of generated medical images according to an exemplary embodiment.

FIGS. 10A and 10B are a diagram showing an example of generated medical images according to an exemplary embodiment.

Referring to FIG. 10A, a medical imaging apparatus may display a Doppler image 1024 and a still ultrasound image 1014 in a D only mode. In this case, the Doppler image 1024 corresponds to Doppler data for a sample volume set on the ultrasound image 1014. If a user command for moving a location of the sample volume is input when the medical imaging apparatus is in a D only mode (i.e., the medical imaging apparatus receives a user input for moving the location of the sample volume), the medical imaging apparatus may change an operating mode to a 2D only mode such as a B-mode. In other words, if a user moves a location of the sample volume by using a track ball when the medical imaging apparatus displays the Doppler image 1024, as shown in FIG. 10A, the medical imaging apparatus may display an ultrasound image 1012 that is updated in real-time (or almost in real-time) as shown in FIG. 10B. In this case, generation of a Doppler image 1022 is suspended. If a time period during which a user input related to a sample volume is not received is greater than or equal to a threshold value when the ultrasound image 1012 is displayed as shown in FIG. 10B, the medical imaging apparatus may change an operating mode back to the D only mode. Thus, the medical imaging apparatus may display a Doppler image 1024 for a new sample volume.

Figure 11:
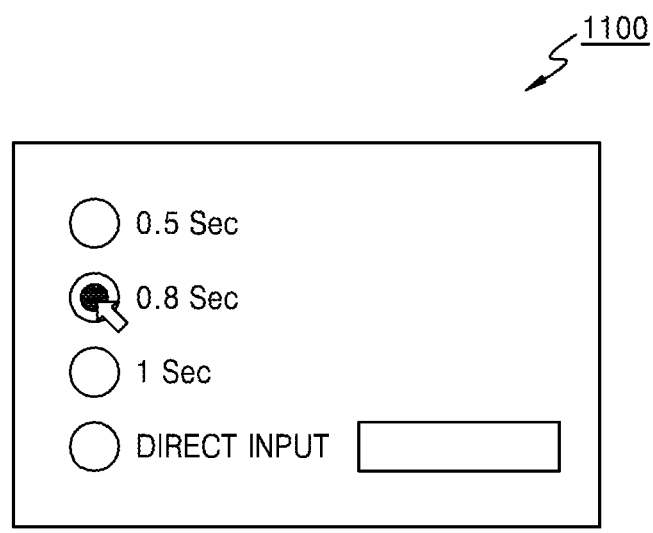
FIG. 11 is an exemplary diagram of a user interface displayed by a medical imaging apparatus according to an exemplary embodiment.

In this case, the threshold value may be preset in the medical imaging apparatus or selected by the user. FIG. 11 is an exemplary diagram of a user interface 1100 displayed by a medical imaging apparatus according to an exemplary embodiment. Referring to FIG. 11, the medical imaging apparatus may output the user interface 1100 for selecting a time taken to change a 2D only mode, in which an ultrasound image is displayed, back to a D only mode, in which a Doppler image is displayed. If the user selects the time of 0.8 sec. as shown in FIG. 11, i.e., if the user moves a track ball and then does not manipulate the track ball for 0.8 sec., the medical imaging apparatus may suspend updating of an ultrasound image while generating and displaying a Doppler image for a finally set sample volume.

According to another exemplary embodiment, the medical imaging apparatus may automatically return to a D only mode based on whether a Doppler signal is included in a received signal. For example, if a Doppler signal of which a value is in a normal range is detected from received signals acquired by a data acquisition unit of the medical imaging apparatus when the ultrasound image (1012 of FIG. 10B) is displayed, the medical imaging apparatus may suspend updating of the ultrasound image 1012 and display the Doppler image 1024 again, as shown in FIG. 10A.

Exemplary embodiments may be implemented through computer-readable recording media having recorded thereon computer-executable instructions such as program modules that are executed by a computer. Computer-readable media may be any available media that can be accessed by a computer and include both volatile and nonvolatile media and both detachable and non-detachable media. Furthermore, the computer-readable media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and they include any information transmission media.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. A method of generating a medical image by using a medical imaging apparatus, the method comprising:
   acquiring received signals;
   acquiring a first ultrasound image and displaying the first ultrasound image, wherein the first ultrasound image exhibits a tissue structure proximate to a sample volume;
   acquiring a first Doppler signal corresponding to the sample volume set on the first ultrasound image;
   generating a first Doppler image based on the first Doppler signal and displaying the first Doppler image simultaneously with the first ultrasound image, wherein the first Doppler signal indicates by position on a graph different intensity levels of different velocities of a body fluid associated with the sample volume;
   calculating at least one selected from an average magnitude, a maximum value, and a minimum value of the first Doppler signal;
   determining the at least one selected from the average magnitude, the maximum value, and the minimum value of the first Doppler signal is less than a threshold value thereof; and
   when the at least one selected from the average magnitude, the maximum value, and the minimum value of the first Doppler signal is less than the threshold value thereof, acquiring a second ultrasound image by updating the first ultrasound image, displaying the second ultrasound image, and suspending the displaying of the first Doppler image.

2. The method of claim 1, wherein the first Doppler image comprises at least one of a color Doppler image and a Pulsed Wave (PW) Doppler image.

3. The method of claim 1, wherein the updating of the first ultrasound image comprises:
   determining the first Doppler signal is included in the received signals; and
   changing an image displaying mode by suspending the updating of the first ultrasound image and displaying the first Doppler image again, in response to the first Doppler signal being included in the received signals.

4. A medical imaging apparatus comprising:
   an ultrasound transceiver configured to transmit ultrasound signals to an object and receive ultrasound echo signals reflected from the object;
   at least one processor configured to:
   acquire received signals based on the ultrasound echo signals received from the ultrasound transceiver,
   generate a first ultrasound image based on the received signals, wherein the first ultrasound image exhibits a tissue structure proximate to a sample volume;
   select a Doppler signal corresponding to the sample volume set on the first ultrasound image from among the received signals, generate Doppler data based on the Doppler signal, wherein the Doppler signal indicates by position on a graph different intensity levels of different velocities of a body fluid associated with the sample volume,
   generate a Doppler image based on the Doppler data,
   calculate at least one selected from an average magnitude, a maximum value, and a minimum value of the Doppler signal, and
   determine the at least one selected from the average magnitude, the maximum value, and the minimum value of the Doppler signal is less than a threshold value thereof; and
   a display configured to, display the first ultrasound image, and display the Doppler image,
   wherein when the at least one selected from the average magnitude, the maximum value, and the minimum value of the Doppler signal is less than the threshold value thereof, the at least one processor is configured to acquire a second ultrasound image by updating the first ultrasound image, and the display is configured to display the second ultrasound image and suspend the displaying of the Doppler image, and
   wherein the display is configured to display the Doppler image simultaneously with the first ultrasound image.

5. The medical imaging apparatus of claim 4, wherein the at least one processor suspends the updating of the first ultrasound image and generates the Doppler data again, in response to the Doppler signal being included in the received signals.

6. A non-transitory computer-readable recording medium including program code that, when executed by one or more processors, causes a medical imaging apparatus to:
   acquire received signals;
   acquire a first ultrasound image and display the first ultrasound image, wherein the first ultrasound image exhibits a tissue structure proximate to a sample volume;
   acquire a Doppler signal corresponding to the sample volume set on the first ultrasound image;
   generate a Doppler image based on the Doppler signal and display the generated Doppler image simultaneously with the first ultrasound image, wherein the Doppler signal indicates by position on a graph different intensity levels of different velocities of a body fluid associated with the sample volume;
   calculate at least one selected from an average magnitude, a maximum value, and a minimum value of the Doppler signal; and
   determine the at least one selected from the average magnitude, the maximum value, and the minimum value of the Doppler signal is less than a threshold value thereof, and acquire a second ultrasound image by updating the first ultrasound image, display the second ultrasound image, and suspend the displaying of the Doppler image when the at least one selected from the average magnitude, the maximum value, and the minimum value of the Doppler signal is less than the threshold value thereof.

7. The method of claim 1, further comprising:

when the at least one selected from the average magnitude, the maximum value, and the minimum value of the first Doppler signal is less than the threshold value thereof, acquiring a second Doppler signal corresponding to a sample volume set on the second ultrasound image;

generating a second Doppler image based on the second Doppler signal and displaying the second Doppler image;

calculating at least one selected from an average magnitude, a maximum value, and a minimum value of the second Doppler signal;

determining whether the at least one selected from the average magnitude, the maximum value, and the minimum value of the second Doppler signal is less than a threshold value thereof; and when the at least one selected from the average magnitude, the maximum value, and the minimum value of the second Doppler signal is greater than or equal to the threshold value thereof, continuously displaying the second ultrasound image and the second Doppler image.

8. The medical imaging apparatus of claim 4, wherein the Doppler image comprises at least one of a color Doppler image and a Pulsed Wave (PW) Doppler image.

* * * * *